US009019479B2

(12) United States Patent
Nagai et al.

(10) Patent No.: US 9,019,479 B2
(45) Date of Patent: Apr. 28, 2015

(54) IMAGING APPARATUS AND IMAGE PROCESSING METHOD

(71) Applicant: Canon Kabushiki Kaisha, Tokyo (JP)

(72) Inventors: Kentaro Nagai, Yokohama (JP); Mitsuo Takeda, Chofu (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/347,270

(22) PCT Filed: Nov. 2, 2012

(86) PCT No.: PCT/JP2012/079051
§ 371 (c)(1),
(2) Date: Mar. 26, 2014

(87) PCT Pub. No.: WO2013/073453
PCT Pub. Date: May 23, 2013

(65) Prior Publication Data
US 2014/0241632 A1 Aug. 28, 2014

(30) Foreign Application Priority Data
Nov. 14, 2011 (JP) .................................. 2011-248717

(51) Int. Cl.
*G01C 3/08* (2006.01)
*G06K 9/62* (2006.01)
(Continued)

(52) U.S. Cl.
CPC ... *G06K 9/62* (2013.01); *A61B 6/00* (2013.01); *A61B 6/484* (2013.01); *A61B 6/5258* (2013.01);
(Continued)

(58) Field of Classification Search
USPC .............. 356/4.09, 28.5, 35.5, 450, 460, 477, 356/900; 382/190; 359/370, 489.19, 577; 250/227.11, 358.1
See application file for complete search history.

(56) References Cited

U.S. PATENT DOCUMENTS

| 5,424,743 A * | 6/1995 | Ghiglia et al. ............... 342/25 C |
| 5,481,356 A * | 1/1996 | Pouet et al. .................. 356/35.5 |
| 7,538,891 B1 * | 5/2009 | Mello et al. .................. 356/520 |

(Continued)

FOREIGN PATENT DOCUMENTS

WO 2010/146503 A1 12/2010

OTHER PUBLICATIONS

Notification of and International Preliminary Report on Patentability completed May 20, 2014, and mailed on May 30, 2014, in counterpart International Patent Application No. PCT/JP2012/079051.
Kottler et al., "A two-directional approach for grating based differential phase contrast imaging using hard x-rays," Optics Express, vol. 15, No. 3, Feb. 5, 2007, pp. 1175-1181.
(Continued)

*Primary Examiner* — Samir Ahmed
(74) *Attorney, Agent, or Firm* — Fitzpatrick, Cella, Harper & Scinto (57) ABSTRACT

Disclosed is an imaging apparatus for generating data of a phase image based on an interference pattern acquired by a shearing interferometer, including: a differential phase data calculating unit that calculates first differential phase data expressing a change of a phase in a first direction and second differential phase data expressing a change of a phase in a second direction, based on interference pattern data generated by an electromagnetic wave transmitted through a subject; a second-order differential phase data calculating unit that calculates first second-order differential phase data by differentiating the first differential phase data in the first direction, and calculates second second-order differential phase data by differentiating the second differential phase data in the second direction; and a phase data calculating unit that calculates the phase image by solving a second-order differential equation including the first and second second-order differential phase data as functions.

12 Claims, 10 Drawing Sheets

(51) Int. Cl.
*A61B 6/00* (2006.01)
*G01N 23/04* (2006.01)
*G01J 9/02* (2006.01)

(52) U.S. Cl.
CPC .......... *G01N 23/04* (2013.01); *G01N 2223/345* (2013.01); *G01N 2223/401* (2013.01); *G01J 9/0215* (2013.01)

(56) References Cited

U.S. PATENT DOCUMENTS

| | | | |
|---|---|---|---|
| 7,619,719 B2 * | 11/2009 | Rohner et al. | 356/4.09 |
| 2004/0069949 A1 | 4/2004 | Sakaida | |
| 2009/0073563 A1 * | 3/2009 | Betzig | 359/578 |
| 2012/0105858 A1 * | 5/2012 | Popescu et al. | 356/450 |

* cited by examiner

IMAGING APPARATUS AND IMAGE PROCESSING METHOD

TECHNICAL FIELD

The present invention relates to a technique to generate data for a phase image and a differential phase image from an interference pattern acquired by a shearing interferometer.

BACKGROUND ART

A searing interferometer is means of visualizing a phase change of light, caused by a subject, using a shift of fringes. The fringes are generated by separating coherent light, such as beams irradiated from a single light source, generating distortion of wavefronts in one beam by the subject, and slightly shifting the other beam. This searing interferometer is used, for example, for improving the visibility of a subject in the field of phase contrast microscopes.

As a shearing interferometer, an interferometer using Talbot interferometry is known.

According to the Talbot interferometry, light from a light source is irradiated onto a subject, and light, of which phase is changed by transmitting through the subject, is guided to a diffraction grating. The light diffracted by the diffraction grating forms an interference pattern in a position that is a predetermined distance (Talbot distance) away from the diffraction grating. In the case of using an x-ray, directly detecting an interference pattern may be difficult, since the period of the interference pattern is very short. A method that is proposed to solve this problem is disposing an absorption grating in a position where the interference pattern is formed, generating moiré by interrupting a part of the interference pattern by the absorption grating, and detecting this moiré image using a detector. The information on the phase of the subject can be acquired by analyzing this moiré image. The imaging using a phase of light like this is generally called phase imaging (x-ray phase imaging if an x-ray is used).

However what can be directly analyzed by the interference pattern is a spatial differential amount of a phase of light that is changed by transmitting through the subject (also called differential phase image or shear image).

Since spatial differentiation has the effect to enhance edges, a differential phase image is used for enhancing an image of a subject in the field of optical microscopes or the like. An original phase can be calculated based on the differential phase image, so as to acquire the original phase image.

NPL 1 discloses an x-ray phase imaging method using two-dimensional Talbot interferometry. In concrete terms, a differential phase image in the X direction and a differential phase image in the Y direction are acquired from an interference pattern generated by two-dimensional diffraction grating, and a phase image is calculated by performing Fourier-domain integration method on these differential phase images.

CITATION LIST

Non-Patent Literature

[NPL 1] C. Kottler, C. David, F. Pfeiffer and O. Bunk, "A two-directional approach for grating based differential phase contrast imaging using hard x-rays," Optics Express 15 (2007), 1175-1181

SUMMARY OF INVENTION

Phase imaging using a shearing interferometer can be applied to image diagnosis and various non-destructive inspections. X-ray phase imaging in particular attracts attention as a new image diagnostic method, because compared with a conventional method of imaging the x-ray absorption amount, such as CT (Computer Tomography), the exposure dosage can be dramatically decreased, and such soft tissue as muscle and internal organs can be imaged.

In this kind of phase imaging, a fundamental problem is how to improve the image quality with decreasing noises and artifacts. In the case of using an x-ray as a light source in particular, generating quantum noises is inevitable, and noises have a tendency to increase as the a dose is decreased in order to decrease exposure dosage, so an anti-noise measure is critical. Even if the apparatus uses a visible light, not x-rays, only low quantity light can be used in some cases depending on an inspection target (e.g. eye ball), where deterioration of the S/N ratio is the problem.

In phase imaging, a problem called "phase wrapping" is known. Phase wrapping is a phenomenon where a differential phase value acquired from an interference pattern is wrapped in the $2\pi$ range. For example, if the differential phase value is wrapped in the $-\pi$ to $\pi$ range, an actual correct value of the phase $(3/2)\pi$ is measured as $(-1/2)\pi$. This phase wrapping problem is ignored in NPL 1. Therefore in a phase image generated using the method disclosed in NPL 1, a strain of phase or an artifact may appear in a space where nothing should exist, that is, a space where a phase is constant.

A known countermeasure to phase wrapping is processing called "phase unwrapping". Phase unwrapping is an operation to detect a location where a phase is wrapped, and return the phase to its original state. Various methods have been proposed for phase unwrapping. The most basic operation is calculating a difference from a phase of an adjacent pixel. If the absolute value of the difference is a predetermined value or more (e.g. $(3/2)\pi$ or more), the location can be suspected as a phase-wrapped location where a phase was smooth and continuous in the original state, and an operation to return the phase to its original state is performed. In concrete terms, $2\pi$ or $-2\pi$ is added to the phases of the pixel where the phase jump occurred and all the pixels thereafter, so that the phase difference from the adjacent pixel becomes at most $(3/2)\pi$. Conventional phase unwrapping must be applied to the entire differential phase image as an operation that is independent from the integration, hence a long processing time is required to acquire the phase image.

With the foregoing in view, it is an object of the present invention to provide a technique in the phase imaging to generate a high quality phase image or a differential phase image with less noise.

It is another object of the present invention to provide a technique in the phase imaging to implement the reduction of noise in a phase image or a differential phase image, and suppress the strain of a phase and artifact caused by phase wrapping using simple processing.

A first aspect of the present invention is an imaging apparatus for generating data or a phase image based on an interference pattern acquired by a shearing interferometer, comprising: a differential phase data calculating unit that calculates first differential phase data expressing a change of a phase in a first direction and second differential phase data expressing a change of a phase in a second direction which intersects the first direction, based on data of an interference pattern generated by an electromagnetic wave transmitted through a subject; a second-order differential phase data calculating unit that calculates first second-order differential phase data by differentiating the first differential phase data in the first direction, and calculates second second-order differential phase data by differentiating the second differential phase data in the second direction; and a phase data calculating unit that calculates the data of the phase image of the subject by solving a second-order differential equation including the first second-order differential phase data and the second second-order differential phase data as functions.

A second aspect of the present invention is an image processing method for generating data of a phase image based on an interference pattern acquired by a shearing interferometer, comprising the steps of: an information processing device calculating first differential phase data expressing a change of a phase in a first direction and second differential phase data expressing a change of a phase in a second direction which intersects the first direction, based on data of an interference pattern generated by an electromagnetic wave transmitted through a subject; the information processing device calculating first second-order differential phase data by differentiating the first differential phase data in the first direction, and calculating second second-order differential phase data by differentiating the second differential phase data in the second direction; and the information processing device calculating the data of the phase image of the subject by solving a second-order differential equation including the first second-order differential phase data and the second second-order differential phase data as functions.

A third aspect of the present invention is a program for causing an information processing device to execute each step of the above mentioned image processing method.

According to the present invention, in the phase imaging, a high quality phase image or differential phase image with less noise can be generated. Furthermore, in the phase imaging, the reduction of noise in a phase image or a differential phase image and control of the strain of a phase and artifact caused by phase wrapping can be implemented using simple processing.

Further features of the present invention will become apparent from the following description of exemplary embodiments with reference to the attached drawings.

DESCRIPTION OF EMBODIMENTS

Preferred embodiments of the present invention will now be described with reference to the accompanying drawings.

In each drawing, same composing elements are denoted with a same reference numeral, where redundant description is omitted.

In the present embodiment, an example of using an x-ray Talbot interferometer as means of acquiring a differential phase image will be described. A method for acquiring a differential phase image, to which the present invention can be applied, is not limited to this method, but any shearing interferometer can be used only if a differential phase image of a subject (test object) can be acquired. Light used for measurement is not limited to an x-ray, but may be an electromagnetic wave having any wavelength. An x-ray in this description refers to light of which energy is at least 2 keV and at most 200 keV.

(Configuration of Imaging Apparatus)

Figure 1:
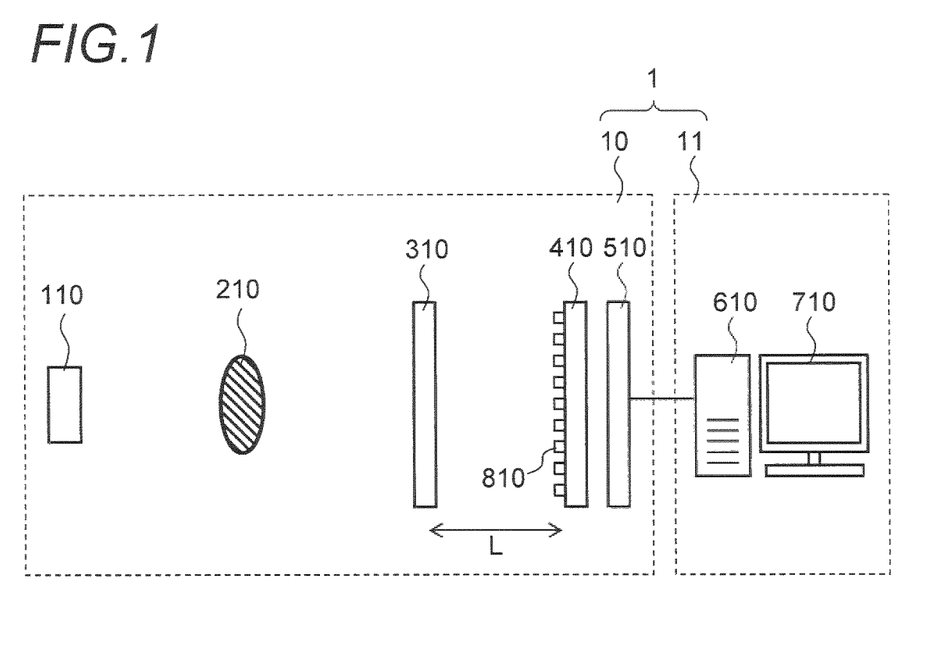
FIG. 1 is a diagram depicting a configuration of an imaging apparatus.

FIG. 1 is a diagram depicting a configuration of an imaging apparatus according to this embodiment. The imaging apparatus 1 shown in FIG. 1 is roughly constituted by an interferometer 10 and an information processing device 11. The interferometer 10 is a two-dimensional x-ray Talbot interferometer, and comprises an x-ray source (light source) 110 that generates x-rays, a diffraction grating 310 that diffracts an x-ray, an absorption grating 410 that interrupts a part of an x-ray, and a detector 510 that detects an x-ray. The information processing device 11 comprises a computing unit (computer main unit) 610 and an image display apparatus 710. The information processing device 11 is connected to the interferometer 10 via a cable so as to control each unit of the interferometer 10. The data of the interference pattern acquired by the detector 510 of the interferometer 10 is transferred to the information processing device 11, and is provided for various later mentioned computation processing in the computing unit 610.

The image based on the computing result by the computing unit 610 is outputted to the image display apparatus 710.

The subject 210, which is a measurement target, is disposed between the x-ray source 110 and the diffraction grating 310. The x-ray that was irradiated from the x-ray source 110 and transmitted through the subject 210 is diffracted by the diffraction grating 310, and forms an interference pattern 810, in which a bright portion and a dark portion are arrayed on a surface that is positioned a predetermined distance L called Talbot distance, away from the diffraction grating 310. In this description, a bright portion indicates where intensity of the x-ray (light) is high, and a dark portion indicates where intensity of the x-ray is low. The diffraction grating 310 used for this embodiment is a phase type diffraction grating. For the diffraction grating, an amplitude diffraction grating may be used, but a phase type diffraction grating has more of an advantage, since loss of an x-ray amount (quantity of light) is low. A differential phase image can also be acquired from the interference pattern 810 by disposing the subject between the diffraction grating 310 and the absorption grating 410, although this configuration is different from this embodiment.

Figure 2A:
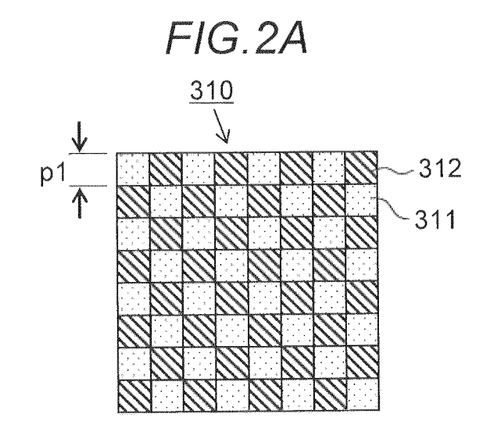
FIGS. 2A to 2C show configuration examples of a diffraction grating, an interference pattern and an absorption grating.
Figure 2B:
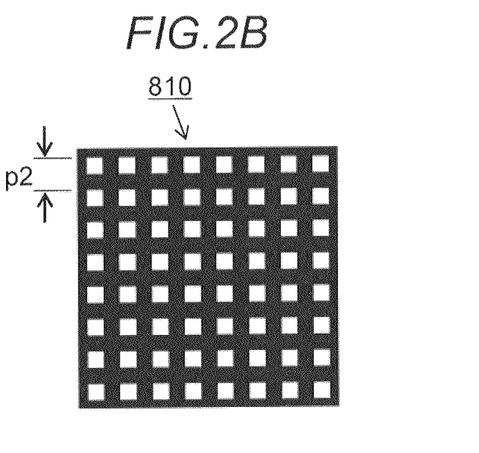

FIG. 2A shows an example of a configuration of the phase type diffraction grating 310 (hereafter simply called phase grating 310) on a plane. 311 is an area to be a reference of the phase, and 312 is an area where the phase of the x-ray changes by $\pi$ from the reference area 311. FIG. 2B shows a bright portion and a dark portion of an interference pattern 810 that is generated at the Talbot distance by the phase grating 310. There are several types of combinations between the phase grating 310 and the interference pattern 810, but any configuration, including those publically known, can be used in the present invention, hence detailed description thereof is omitted here.

Generally there are two methods to acquire data of the differential phase image (differential phase data) from the interference pattern 810. One is a fringe scanning method, in which the pattern is imaged a plurality of times while shifting the absorption grating 410 little by little, and the differential phase data is calculated based on these results. The other is a Fourier transform method, in which the absorption grating 410, of which period is slightly shifted from an interference pattern 810 as a self image, is used. The Fourier transform method will be described herein below, but both methods can be used for this embodiment, since the differential phase data can be acquired by either method. The absorption grating may be called a screen grid or an amplitude grating.

Figure 2C:
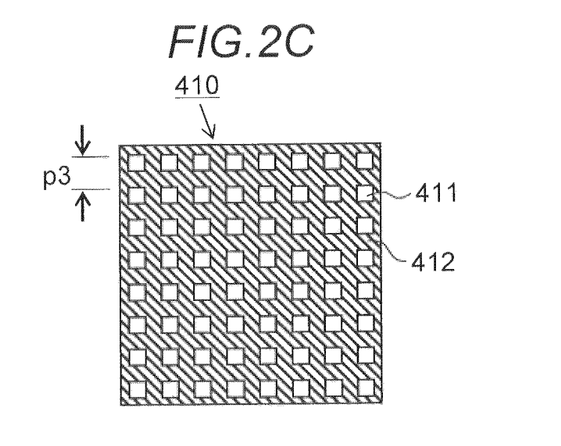

In the Fourier transform method, an absorption grating 410 shown in FIG. 2C is used. In the absorption grating 410, a transmitting portion 411, corresponding to the bright portion of the interference pattern 810 and a blocking portion 412 corresponding to the dark portion thereof, are formed. The period (pitch) of the transmitting portion 411 is different from the period of the bright portion of the interference pattern 810. Therefore if the image of light that transmitted through the absorption grating 410 is actually captured, moiré is generated because of the difference of the periods between the interference pattern 810 and the absorption grating 410.

Normally the period of the interference pattern 810, generated by the phase grating 310, is about several μm to dozen μm, but this period can be expanded to at least several tens μm by generating moiré using the absorption grating 410. Thereby the interference pattern can be imaged using a detector 510 of which resolution is about several tens μm. However in the case when the detector 510 can resolve the interference pattern 810 itself, such as a case of the detector 510 having sufficiently high resolution or a case of the distance between the phase grating 310 and the detector 510 being long, the absorption grating 410 is not necessary.

(Function of Information Processing Device)

Figure 3:
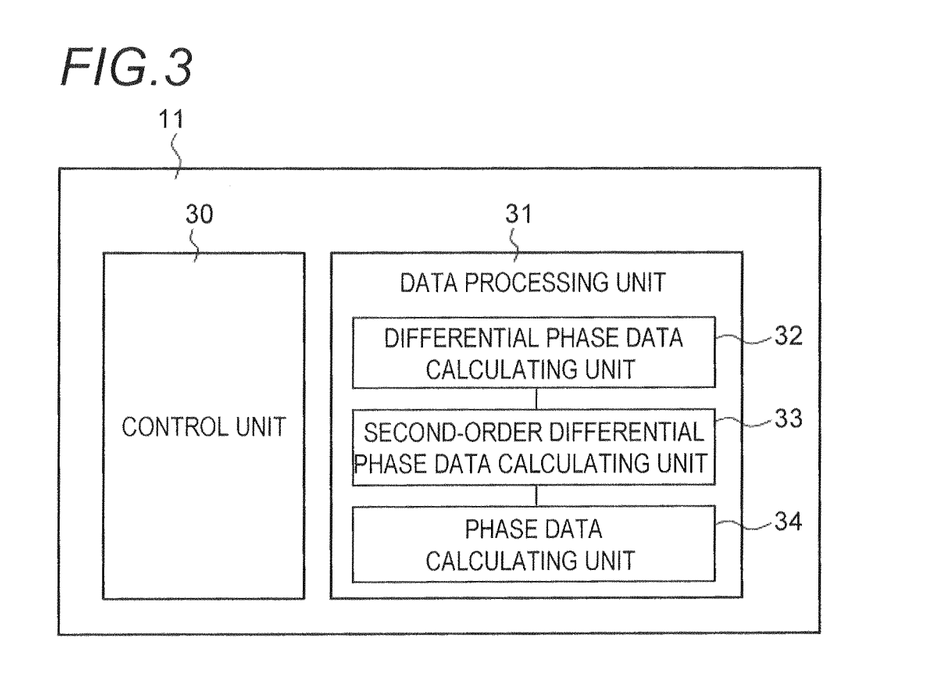
FIG. 3 is a diagram depicting a functional configuration of an information processing device.

FIG. 3 is a block diagram depicting a function of the computing unit 610 of the information processing device 11. The computing unit 610 has a control unit 30 that controls the interferometer 10 (e.g. irradiation of x-rays, loading data from detector 510), and a data processing unit 31 that generates data of a phase image based on the data loaded from the interferometer 10. The data processing unit 31 is comprised of a differential phase data calculating unit 32, a second-order differential phase data calculating unit 33, and a phase data calculating unit 34. The differential phase data calculating unit 32 has a function to numerically analyze the data of the interference pattern (moiré image) and calculate the differential phase data, and the second-order differential data calculating unit 33 has a function to calculate second-order differential phase data by differentiating the differential phase data. The phase data calculating unit 34 has a function to calculate data of a phase image of a subject (phase data) by solving a second-order differential equation including the second-order differential phase data as a function. These functions will be described in detail later.

The computing unit 610 of the information processing device 11 comprises a CPU (Central Processing Unit), a main storage (e.g. RAM), an auxiliary storage (e.g. HDD, SSD), and a computer having various I/Fs. The functions shown in FIG. 3 are implemented by programs stored in the auxiliary storage that are loaded into the main storage and executed by the CPU. This configuration is merely an example, and does not limit the scope of the present invention.

(Operation of Imaging Apparatus)

Now an image processing method executed in the imaging apparatus 1 of this embodiment and a difference between this method and a prior art will be described. Here as data of the interference pattern, data generated by computer simulation is used rather than data acquired by actually measuring a subject by the interferometer 10. A series of processing steps to generate data of a phase image based on data of the interference pattern is performed by the data processing unit 31 of the information processing device 11.

In the simulation, it is assumed that 17.5 keV monochromatic light is used for the x-rays, and the phase grating 310 having the structure shown in FIG. 2A is used as the phase grating. It is assumed that in the phase grating 310, a columnar structure 312 is arrayed at pitch p1 on a base 311 that sufficiently transmits x-rays. A phase of the x-rays transmitted through the structure 312 changes by π from the x-rays transmitted through the base 311. The phase grating 310 having this structure is implemented by setting the depth to about 22.6 μm if, for example, the structure 312 is made from silicon.

If the pitch p1 is assumed to be 8 μm in FIG. 2A, the interference pattern 810 is formed on the absorption grating 410 by setting the distance L between the phase grating 310 and the absorption grating 410 in FIG. 1 to approximately 11.3 cm. The period p2 of this interference pattern 810 is 4 μm. The interference pattern 810 is expanded by generating moiré by the absorption grating 410, and the intensity thereof is detected by the detector 510. The size of the pixel element included in the detector 510 is assumed to be 4 μm to simplify calculation.

In the case of a Talbot interferometer, high coherence is required for the incident light.

To use light with such high coherence in a facility of which size is at most several m, such as in a laboratory or where medical equipment apparatuses are used, a method for generating the coherence using a very small point light source is used.

In this case, the incident light is not a parallel wave, but a spherical wave. This difference however does not alter the essence of the present invention, and the present invention can be applied to both a parallel wave and a non-parallel wave (e.g. spherical wave). In the following example, simulation is performed on the assumption that a parallel wave is used.

Figure 6A:
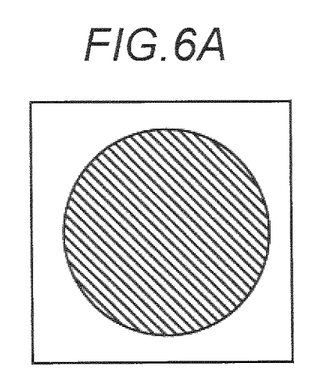
FIGS. 6A to 6D show subjects and differential phase images used for simulation.
Figure 6B:
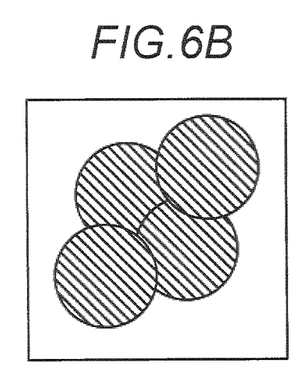

Two types of subjects are provided. One is a calcium ball of which diameter is 400 μm, as shown in FIG. 6A. The other subject is four calcium balls, of which respective diameter is 200 μm, partially overlapping with one another, as shown in FIG. 6B. The range of calculation is 512 μm×512 μm.

As a method to acquire differential phase data, a Fourier transform method is used, as mentioned above. Therefore the period p3 of the transmitting portion 411 of the absorption grating 410 (see FIG. 2C) is set to 4.5 μm. Thereby moiré of which one period is approximately four pixels is generated.

Figure 4A:
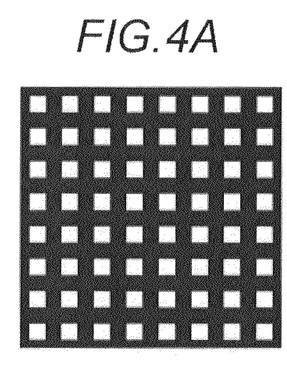
FIGS. 4A to 4D show a method for acquiring differential phase data from an interference pattern.
Figure 4B:
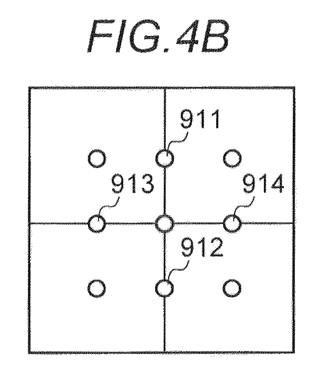
Figure 4C:
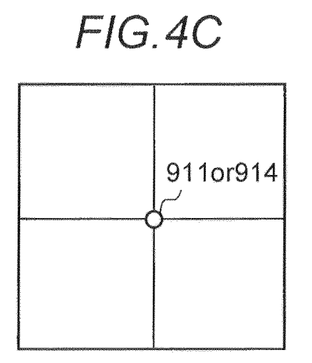
Figure 4D:
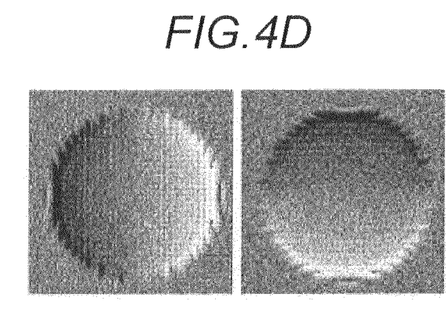

FIG. 4A to FIG. 4D are conceptual diagrams depicting a method for acquiring differential phase data from the interference pattern according to a Fourier transform method, in other words, the processing content of the differential phase data calculating unit 32. It is assumed that a moiré image shown in FIG. 4A is acquired as a result of expanding the interference pattern 810 in FIG. 2B. In the Fourier transform method, this moiré image is Fourier-transformed. As a result, it is separated into nine spectra in the Fourier space. Out of the nine spectra, an area including one of the spectra 911, 912, 913 and 914, which are first-order spectra, is extracted using a window function, and the spectrum is returned to its origin (FIG. 4C); and then inverse Fourier transform is performed to acquire the phase differential data. The left side of FIG. 4D is an example of the differential phase image generated from the spectrum 914, and shows a change of the phase in the x direction (first direction). The right side of FIG. 4D is an example of the differential phase image generated from the spectrum 911, and shows a change of the phase in the y direction (second direction).

Figure 6C:
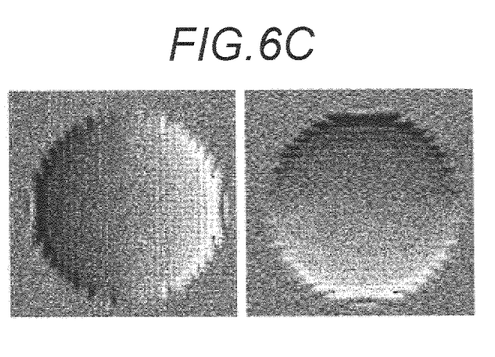
Figure 6D:
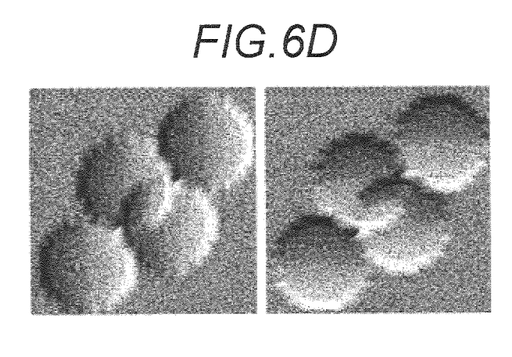

FIG. 6C shows differential phase images in the x direction and the y direction acquired from the subject shown in FIG. 6A. FIG. 6D shows differential phase images in the x direction and the y direction acquired from the subject shown in FIG. 6B. The edge portion of a sphere is where the differentiation of the phase changes most sharply, hence phase jump tends to be generated in this portion. Further, in the case of the Fourier transform method, artifact (an image that should not exist) may be generated in the differential phase image, depending on how the window function is set. Some artifacts are also observed in the differential phase images in FIG. 6C and FIG. 6D.

In the case of two-dimensional data, the differential phase data in the x direction and that in the y direction can be acquired independently. Which direction data is acquired can be controlled by a choice of the spectrum to be extracted in the Fourier space in FIG. 4B. For example, if the spectrum 911 or 912 is extracted, the differential phase data in the y direction is acquired, and if the spectrum 913 or 914 is extracted, the differential phase data in the x direction is acquired. Needless to say, differential phase data can be acquired in any two directions that intersect with each other, and is not limited to the two orthogonally intersecting directions of x and y. Hereafter the acquired x direction differential phase data is denoted with $\phi_x(x,y)$, and the y direction differential phase data is denoted with $\phi_y(x,y)$, (x,y) are coordinates. Integrated phase data is determined based on the x direction differential phase data and the y direction differential phase data.

(1) Conventional Phase Data Acquisition Method

In the prior art, the x direction differential phase data and the y direction differential phase data are independently integrated, or are integrated using such a method as Fourier transform, so as to acquire the phase data. An integration method using Fourier transform (Fourier-domain integration method), which can determine a phase with less error, will be described herein below as a prior art.

Figure 9:
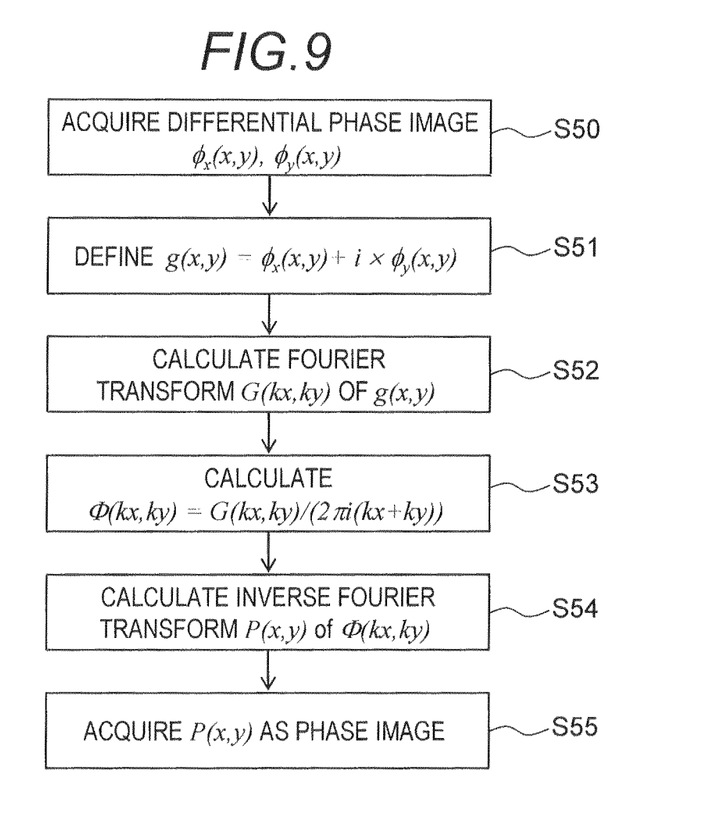
FIG. 9 is a flow chart depicting processing to calculate a phase image based on data of a differential phase image according to a prior art.

FIG. 9 is a flow chart depicting a procedure of the phase data acquisition method based on the Fourier integration method. As mentioned above, the x direction differential phase data $\phi_x(x,y)$ and the y direction differential phase data $\phi_y(x,y)$ are calculated first (step S50). g(x,y) is defined by the following expression (step S51).

$$g(x,y) = \phi_x(x,y) + i \times \phi_y(x,y) \quad \text{(Expression 1)}$$

Here i denotes a imaginary unit.

By performing Fourier transform on g(x,y), G(kx,ky) is acquired (step S52), and phase P(x,y) is calculated using the following (Expression 3) (steps S53, S54).

$$G(k_x, k_y) = F[g(x, y)] \quad \text{(Expression 2)}$$

$$P(x, y) = F^{-1}\left[\frac{G(k_x, k_y)}{2\pi i \times (k_x + k_y)}\right] \quad \text{(Expression 3)}$$

Here F[ . . . ] denotes an operator that indicates Fourier transform is performed inside the bracket, and $F^{-1}$[ . . . ] denotes an operator that indicates inverse Fourier transform is performed inside the bracket. kx and ky denotes a wave number in the x direction and a wave number in the y direction respectively. (Expression 3) therefore represents that Fourier transform is performed on g defined by (Expression 1), and then inverse Fourier transform is performed using the integration operator $1/(2\pi i \times (kx+ky))$. P(x,y) acquired like this indicates the phase data of the subject (step S55).

Figure 10A:
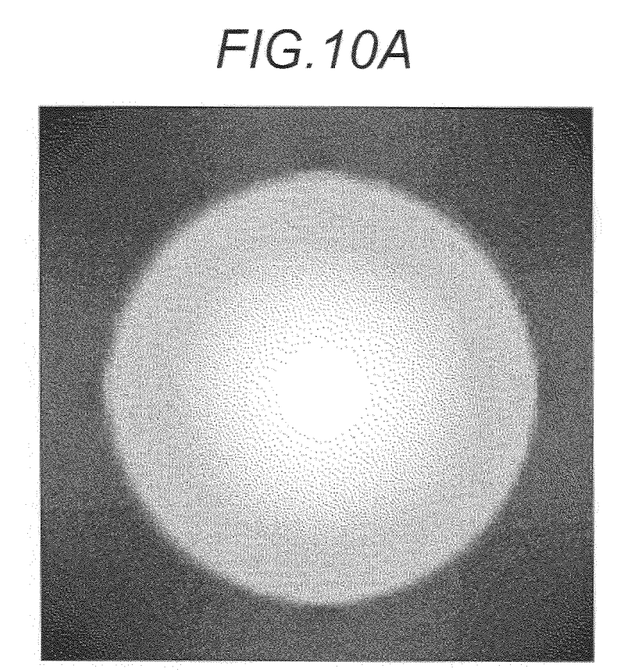
FIGS. 10A and 10B show phase images acquired according to the method of the prior art.

FIG. 10A is an example of a phase image acquired by the method of the prior art shown in FIG. 9 based on the data of the differential phase image shown in FIG. 6C. The phase of the calcium ball has been restored to be a ball. However because of phase wrapping, the phase is discontinuous in an outer circumference portion of the subject, and strain has been generated in the acquired phase image. In particular, strain of the phase, which should not exist, is generated in the outer circumference portion of the subject, which should be a vacuum portion (constant phase).

Figure 10B:
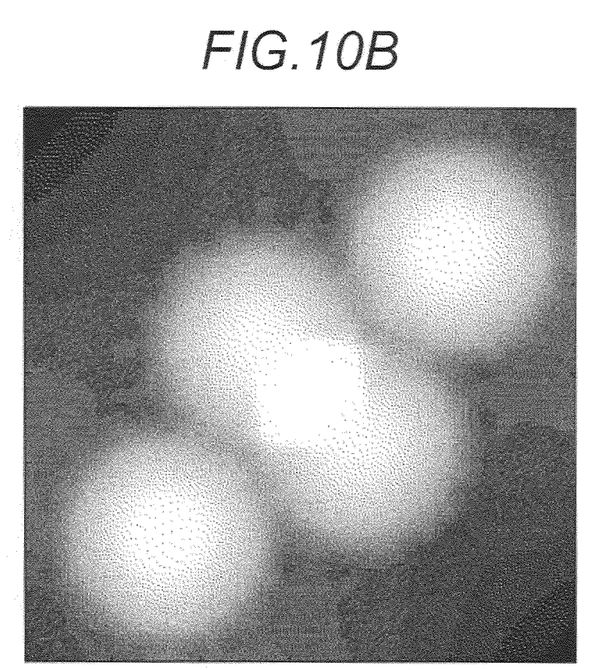

FIG. 10B is an example of a phase image acquired by the method of the prior art shown in FIG. 9 based on the data of the differential phase image shown in FIG. 6D. The phase of the four calcium balls has been restored.

However just like the previous example, the strain of the phase has been generated in an area that should be a vacuum. Furthermore the phase that should be a ball appears to have jaggies due to the influence of an artifact.

(2) Phase Data Acquisition Method of Embodiment

Figure 5:
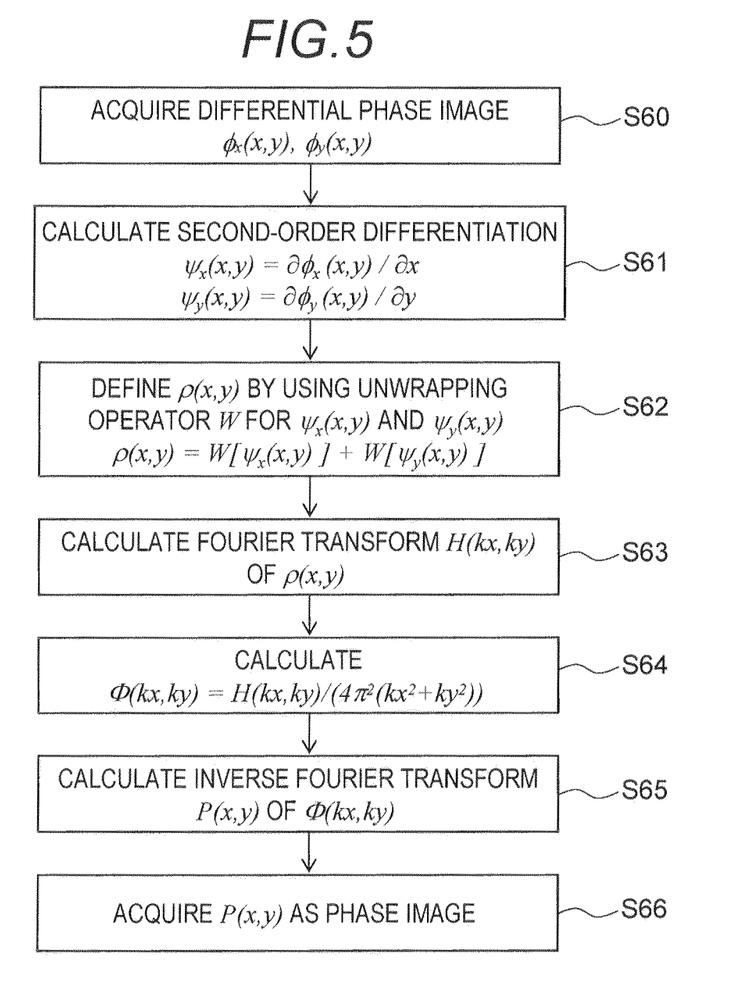
FIG. 5 is a flow chart depicting processing to calculate phase data based on differential phase data according to an embodiment.

FIG. 5 is a flow chart depicting a procedure of a phase data acquisition method according to the embodiment of the present invention.

The phase data is acquired by directly integrating the differential phase data in the prior art, but according to this embodiment, second-order differential phase data is generated first by differentiating the differential phase data for the x direction and the y direction respectively, then the phase data is acquired by solving the second-order differential equation based on the second-order differential phase data.

First the differential phase data calculating unit 32 calculates the x direction differential phase data $\phi_x(x,y)$ and the y direction differential phase data $\phi_y(x,y)$ based on the data of the interference pattern (data of the moiré image) (step S60). The x direction differential phase data (first differential phase data) and the y direction differential phase data (second differential phase data) generated by the differential phase data calculating unit 32 are transferred to the second-order differential phase data calculating unit 33.

The second-order differential phase data calculating unit 33 calculates the x direction second-order differential phase data by differentiating the x direction differential phase data in the x direction, and calculates the y direction second-order differential phase data by differentiating the y direction differential phase data in the y direction (step S61). The x direction second-order differential phase data $\psi_x(x,y)$ and the y direction second-order differential phase data $\psi_y(x,y)$ are given by the following expressions.

$$\psi_x(x, y) = \frac{\partial \phi_x(x, y)}{\partial x} \quad \text{(Expression 4)}$$

$$\psi_y(x, y) = \frac{\partial \phi_y(x, y)}{\partial y} \quad \text{(Expression 5)}$$

The x direction second-order differential phase data (first second-order differential phase data) and the y direction second-order differential phase data (second second-order differential phase data) are transferred to the phase data calculating unit 34.

The phase data calculating unit 34 determines the phase data in the x direction and that in the y direction, which are unknown functions, respectively by solving the second-order differential equation including the second-order differential phase data in the x direction and that in the y direction, which are unknown functions (step S62 to S66). This algorithm will now be described in detail.

First the phase data calculating unit 34 defines ρ(x,y) as follows, using the x direction and y direction second-order differential phase data (step S62).

$$\rho(x,y) = W[\psi_x(x,y)] + W[\psi_y(x,y)] \quad \text{(Expression 6)}$$

Here W[ . . . ] denotes an operator to perform processing to confine a value which deviated from a predetermined range into the predetermined range, out of values of [ . . . ]. The values of the differential phase data $\phi_x$ and $\phi_i$ basically are values that change continuously, so the values of the second-order differential phase data $\psi_x$ and $\psi_y$ are confined to a small range (at most $-\pi$ to $\pi$) from 0 as a center. However if phase wrapping is generated, the values of the differential phase data $\phi_x$, $\phi_y$ change discontinuously from $-\pi$ to $\pi$ to $-\pi$, hence the values of the second-order differential phase data $\psi_x$, $\psi_y$ become $2\pi$ or $-2\pi$. In other words, the section where the phase wrapping is generated appears as an abnormal value in a spiking profile in the second-order differential phase data $\psi_x$, $\psi_y$. The operation of W[ . . . ] corresponds to an operation to re-wrap the abnormal values of the second-order differential phase data $\psi_x$, $\psi_y$ into the range from $-\pi$ to $\pi$. Hence W[ . . . ] is called an re-wrapping operator.

Various designs are possible for the re-wrapping operator, but an operator W[ . . . ] having the following rule is used as a concrete and simplest operator in this embodiment.

(a) If the value of [ . . . ] is $\pi$ or greater, $2\pi$ is subtracted from this value.

(b) If the value of [ . . . ] is $-\pi$ or smaller, $2\pi$ is added to this value.

By applying this rule, the same effect as phase unwrapping is exhibited even if phase wrapping is generated in the original functions $\phi_x(x,y)$ and $\phi_y(x,y)$.

In the actual phase unwrapping, not only the above mentioned processing, but also various methods, including processing of singular points generated by noise, are used. For W[ . . . ] as well, various arithmetic algorithms where there processing methods are applied may be used, but the present invention essentially does not depend on these methods, and can be applied to various methods.

The phase data calculating unit 34 calculates the phase P(x,y) by solving the following Poisson's equation based on ρ(x,y) of (Expression 6).

$$\frac{\partial^2 P(x,y)}{\partial x^2} + \frac{\partial^2 P(x,y)}{\partial y^2} = \rho(x,y) \quad \text{(Expression 7)}$$
$$= W[\psi_x(x,y)] + W[\psi_y(x,y)]$$

Various methods are possible as a concrete algorithm to solve the Poisson's equation, and one of these methods is a second-order integration method using Fourier transform. In other words, the phase data calculating unit 34 acquires H(kx, ky) by performing Fourier transform on ρ(x,y) (step S63), and calculates the phase P(x,y) by the following (Expression 9) (steps S64, S65).

$$H(k_x, k_y) = F[\rho(x,y)] \quad \text{(Expression 8)}$$

$$P(x,y) = -F^{-1}\left[\frac{H(k_x, k_y)}{4\pi^2 \times (k_x^2 + k_y^2)}\right] \quad \text{(Expression 9)}$$

In (Expression 9), Fourier transform is performed on ρ(x,y) defined by (Expression 6), then after using the second-order integration operator of $1/(4\pi^2 \times (kx^2 + ky^2))$, inverse Fourier transform is performed, and the calculated value is regarded as phase P(x,y). By this processing, the phase data, that is the second-order integration data of the second-order differential phase data, can be acquired.

Figure 7A:
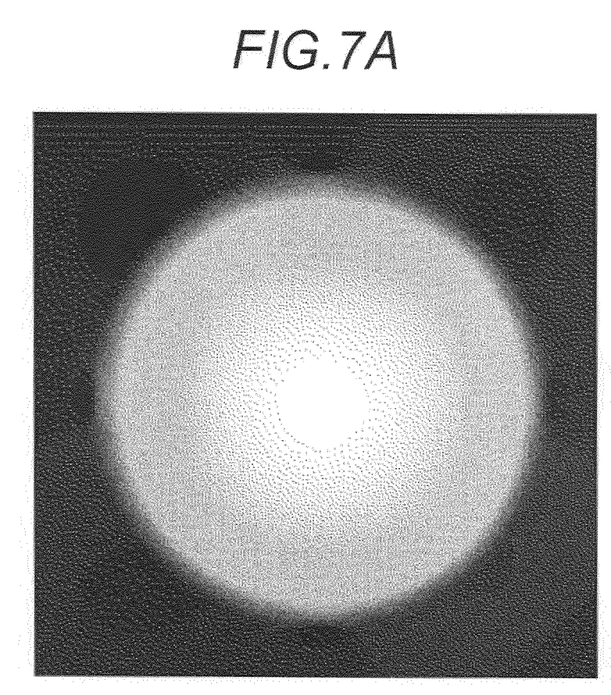
FIGS. 7A to 7B show phase images acquired according to a method of an embodiment.

FIG. 7A is an example of a phase image acquired by the method of this embodiment shown in FIG. 5, based on the data of the differential phase image shown in FIG. 6C. Compared with the prior art in FIG. 10A, strain due to phase wrapping has been improved. This is because the area where the phases are discontinuous in the prior art have been corrected to a degree, indicating the effectiveness of the method of this embodiment.

Figure 7B:
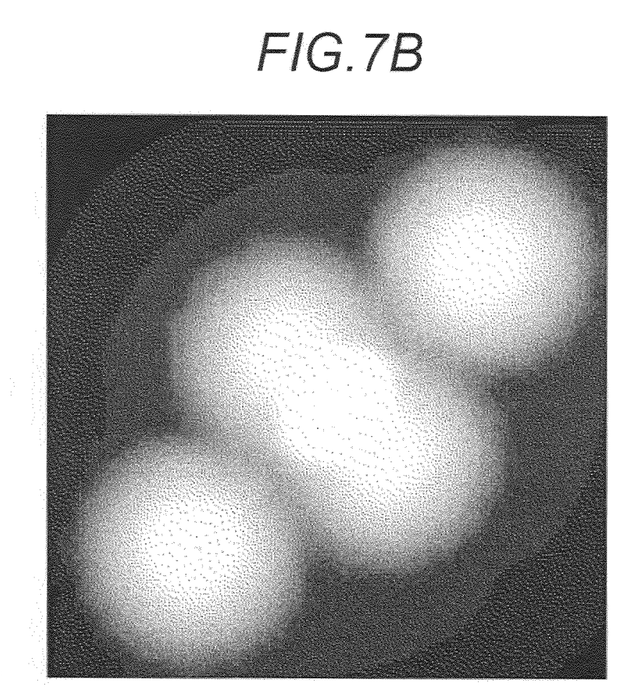

FIG. 7B is an example of a phase image acquired by the method of this embodiment shown in FIG. 5, based on the data of the differential phase image shown in FIG. 6D. Just like the previous example, compared with the prior art in FIG. 10B, strain due to phase wrapping has been improved, indicating the effectiveness of the method of this embodiment. Artifacts that stand out in FIG. 10B of the prior art have also been decreased in FIG. 7B.

The method of this embodiment also excels in noise resistance. Table 1 is a result of comparing the noise reduction functions for a same noise between the phase data acquisition method of the prior art and the phase data acquisition method of this embodiment. In this table, the phase data is calculated regarding two input images including a random pattern noise or which average is 0, and dispersion is 0.5 as differential phase images, and the amount of noise existing in the phase data is compared. In order to evaluate genuine noise reduction, an image that does not include a subject is used in this experiment. The numeric values in Table 1 are dispersion values, and the noise is less (noise has been reduced) as this value becomes smaller. After ten times of calculation, data acquired using the method of this embodiment indicated less noise than that of the method of the prior art each time.

TABLE 1

|  | Prior art | Embodiment | Difference |
| --- | --- | --- | --- |
| First time | 0.6959 | 0.5337 | −0.162 |
| Second time | 0.5339 | 0.5016 | −0.032 |
| Third time | 0.8393 | 0.6545 | −0.185 |
| Fourth time | 0.5518 | 0.4842 | −0.068 |
| Fifth time | 0.6427 | 0.5447 | −0.098 |
| Sixth time | 0.7345 | 0.5954 | −0.139 |
| Seventh time | 0.5777 | 0.5294 | −0.048 |
| Eighth time | 0.5672 | 0.5172 | −0.05 |
| Ninth time | 0.634 | 0.4934 | −0.141 |
| Tenth time | 0.6023 | 0.5756 | −0.027 |

As described above, the method of this embodiment also has a better noise reduction effect than the method of the prior art.

In this experiment, an image which does not include a subject is used, so the effect of this noise reduction is essentially different from the above mentioned image improvement due to phase unwrapping using the re-wrapping operator W.

In other words, even if the phase unwrapping is not performed (that is, even if the operator W is omitted in (Expression 6)), the method of this embodiment has an advantage over the method of the prior art in terms of noise reduction effect.

Figure 8A:
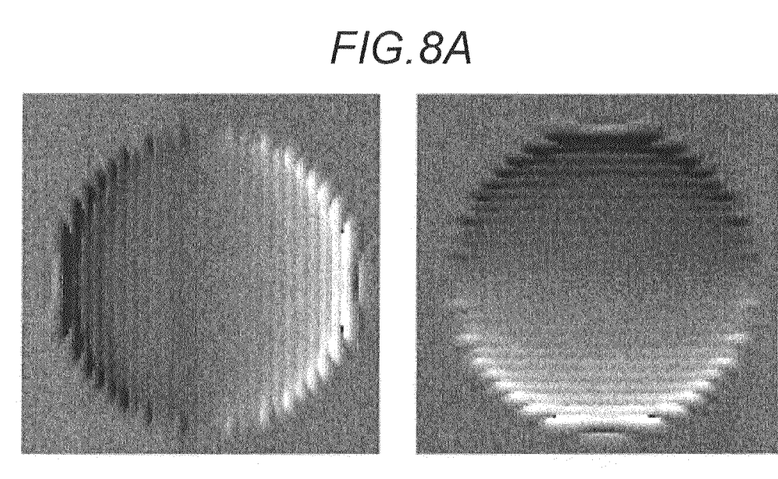
FIGS. 8A and 8B show differential phase images generated from data of the phase images acquired according to the method of the embodiment.
Figure 8B:
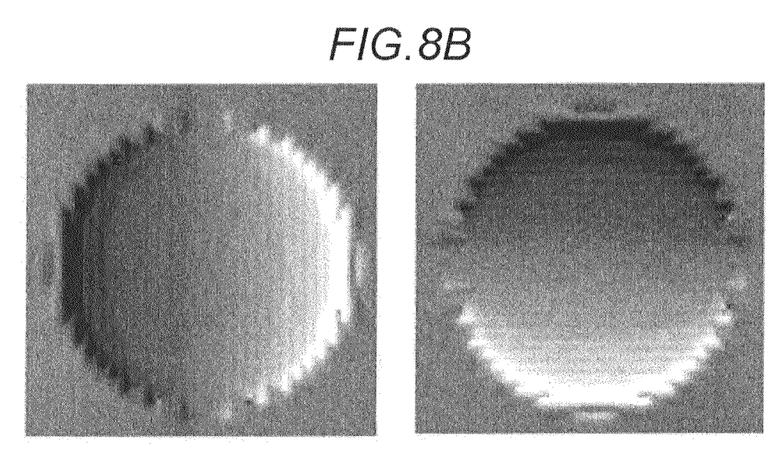

FIG. 8A and FIG. 8B show an application example of the noise reduction effect. FIG. 8A shows differential phase images in the x direction and the y direction, when a noise of which dispersion is 0.25 is superposed on the image of the subject shown in FIG. 6A. FIG. 8B shows differential phase images generated by acquiring phase data from the differential phase image in FIG. 8A using the phase data acquisition method of this embodiment, then differentiating the acquired phase data in the x direction and the y direction respectively. In FIG. 8B, artifacts and noises seen in the original differential phase images in FIG. 8A have been improved, and high quality differential phase images have been acquired. In other words, the method of this embodiment can also be used for the purpose of improving the image quality of a differential phase image. Depending on the content of image diagnosis and inspection, there may be a case when a differential phase image, in which edges are enhanced, may be more useful than a phase image for observation. Therefore a function to generate high image quality differential phase data is very advantageous in a practical sense. This configuration can be implemented by installing a differential phase data calculating unit to differentiate data of a phase image in a subsequent stage of the phase data calculating unit 34 in FIG. 3, for example.

As described above, according to the phase image acquisition method of this embodiment, high quality phase data and differential phase data with less noise can be generated in the phase imaging. By performing the phase unwrapping processing, strain and artifacts of the phase due to phase wrapping can be improved. Furthermore, this embodiment is configured to perform the phase unwrapping processing on the second-order differential phase data, hence the phase unwrapping processing is dramatically simplified and executed at high-speed, compared with the prior art (performing the phase unwrapping processing on the differential phase image). This is because in the case of the second-order differential phase image, a phase jump appears as an abnormal value having a spiking profile, which can be corrected using a simple algorithm, as shown in this embodiment, and also there is no need to check the values of neighboring pixels, which makes it easy to include the algorithm in an integration operation as an operator W.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

The above embodiments and examples are merely concrete examples of the present invention, and are not intended to limit the scope of the claims. For example, in the above embodiments, computation is performed for two orthogonally intersecting directions, but the first direction and the second direction can be arbitrarily set as long as these directions intersect. Further, in the above embodiments, a Talbot interferometer was described as an example, but the present invention can also be applied to other shearing interferometers appropriately.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-248717, filed on Nov. 14, 2011, which is hereby incorporated by reference herein in its entirety.

REFERENCE SIGNS LIST

1 imaging apparatus
10 interferometer
11 information processing device
32 differential phase data calculating unit
33 second-order differential phase data calculating unit
34 phase data calculating unit
210 subject
810 interference pattern

The invention claimed is:

1. An imaging apparatus for generating data of a phase image based on an interference pattern acquired by a shearing interferometer, comprising:
    a differential phase data calculating unit that calculates first differential phase data expressing a change of a phase in a first direction and second differential phase data expressing a change of a phase in a second direction which intersects the first direction, based on data of an interference pattern generated by an electromagnetic wave transmitted through a subject;
    a second-order differential phase data calculating unit that calculates first second-order differential phase data by differentiating the first differential phase data in the first direction, and calculates second second-order differential phase data by differentiating the second differential phase data in the second direction; and
    a phase data calculating unit that calculates the data of the phase image of the subject by solving a second-order differential equation including the first second-order differential phase data and the second second-order differential phase data as functions.

2. The imaging apparatus according to claim 1, wherein the phase data calculating unit performs phase unwrapping processing on the first second-order differential phase data and the second second-order differential phase data when calculating the data of the phase image.

3. The imaging apparatus according to claim 2, wherein the phase unwrapping processing is processing to confine values that deviated from a predetermined range, out of values of the first second-order differential phase data and the second second-order differential phase data, to the predetermined range.

4. The imaging apparatus according to any one of claim 1, wherein the second-order differential equation is an equation to express that a sum of the first second-order differential phase data and the second second-order differential phase data, which are known functions, is equal to a sum of a value generated by performing second-order differentiation on the data of the phase image of the subject, which is an unknown function, in the first direction, and a value generated by performing the second-order differentiation thereon in the second direction.

5. The imaging apparatus according to any one of claim 1, further comprising a differential phase data calculating unit that generates data of a differential phase image of the subject by differentiating the data of the phase image of the subject calculated by the phase data calculating unit.

6. An image processing method for generating data of a phase image based on an interference pattern acquired by a shearing interferometer, comprising the steps of:

an information processing device calculating first differential phase data expressing a change of a phase in a first direction and second differential phase data expressing a change of a phase in a second direction which intersects the first direction, based on data or an interference pattern generated by an electromagnetic wave transmitted through a subject;

the information processing device calculating first second-order differential phase data by differentiating the first differential phase data in the first direction, and calculating second second-order differential phase data by differentiating the second differential phase data in the second direction; and the information processing device calculating the data of the phase image of the subject by solving a second-order differential equation including the first second-order differential phase data and the second second-order differential phase data as functions.

7. A non-transitory computer readable storage medium storing a program for causing an information processing device to execute each step of the image processing method according to claim 6.

8. The imaging apparatus according to claim 2, wherein the second-order differential equation is an equation to express that a sum of the first second-order differential phase data and the second second-order differential phase data, which are known functions, is equal to a sum of a value generated by performing second-order differentiation on the data of the phase image of the subject, which is an unknown function, in the first direction, and a value generated by performing the second-order differentiation thereon in the second direction.

9. The imaging apparatus according to claim 3, wherein the second-order differential equation is an equation to express that a sum of the first second-order differential phase data and the second second-order differential phase data, which are known functions, is equal to a sum of a value generated by performing second-order differentiation on the data of the phase image of the subject, which is an unknown function, in the first direction, and a value generated by performing the second-order differentiation thereon in the second direction.

10. The imaging apparatus according to claim 2, further comprising a differential phase data calculating unit that generates data of a differential phase image of the subject by differentiating the data of the phase image of the subject calculated by the phase data calculating unit.

11. The imaging apparatus according to claim 3, further comprising a differential phase data calculating unit that generates data of a differential phase image of the subject by differentiating the data of the phase image of the subject calculated by the phase data calculating unit.

12. The imaging apparatus according to claim 4, further comprising a differential phase data calculating unit that generates data of a differential phase image of the subject by differentiating the data of the phase image of the subject calculated by the phase data calculating unit.

* * * * *